(12) United States Patent
Barney et al.

(10) Patent No.: US 12,270,063 B2
(45) Date of Patent: Apr. 8, 2025

(54) ALGAL STRAIN AND METHODS FOR PRODUCING SIMPLE SUGARS

(71) Applicant: REGENTS OF THE UNIVERSITY OF MINNESOTA, Minneapolis, MN (US)

(72) Inventors: Brett M. Barney, Minneapolis, MN (US); Evelyn Vogel, Aurora, CO (US); Natalia Calixto Mancipe, Falcon Heights, MN (US)

(73) Assignee: REGENTS OF THE UNIVERSITY OF MINNESOTA, Minneapolis, MN (US)

( * ) Notice: Subject to any disclaimer, the term of this patent is extended or adjusted under 35 U.S.C. 154(b) by 0 days.

(21) Appl. No.: 18/439,199

(22) Filed: Feb. 12, 2024

(65) Prior Publication Data

US 2024/0247292 A1     Jul. 25, 2024

Related U.S. Application Data

(62) Division of application No. 17/870,649, filed on Jul. 21, 2022, now Pat. No. 11,932,889.

(60) Provisional application No. 63/224,948, filed on Jul. 23, 2021.

(51) Int. Cl.
    *C12P 19/02*     (2006.01)
    *C12N 1/12*     (2006.01)
    *C12R 1/89*     (2006.01)

(52) U.S. Cl.
    CPC .............. *C12P 19/02* (2013.01); *C12N 1/125* (2021.05); *C12R 2001/89* (2021.05)

(58) Field of Classification Search
None
See application file for complete search history.

(56) References Cited

U.S. PATENT DOCUMENTS

| | | | |
|---|---|---|---|
| 11,932,889 B2 * | 3/2024 | Barney | C12P 7/22 |
| 2023/0038269 A1 | 2/2023 | Barney et al. | |

OTHER PUBLICATIONS

Arriola et al., "Genome sequence of Chlorella sorokiniana UTEX 1602 and Micractiunium conductrix SAG 241.80: implications to maltose excretion by a green alga" 2017, *Plant J* vol. 93, pp. 566-586.
Barney et al., "Gene Deletions Resulting in Increased Nitrogen Release by Azotobacter vinelandii: Application of a Novel Nitrogen Biosensor" 2015, *Appl Environ Microbiol* vol. 81(13), pp. 4316-4328.
Brechignac et al., Pilot CELSS based on a maltose-excreting Chlorella: concept and overview on the technological developments. *Adv Space Res* 12, 33-36 (1992).
Contreras-Moreira et al., "Analysis of Pant Pan-Genomes and Transcriptomes with Get_Homologues-Est, a Clustering Solution for Sequences of the Same Species" 2017, *Front Plant Sci* vol. 8, No. 184, 16 pages.
Dorling et al., "Effect of pH on growth and carbon metabolism of maltose-releasing Chlorella (Chlorophyta)" 1997, *Eur J Phycol* vol. 32, pp. 19-24.
Ducat et al., "Rerouting Carbon Flux To Enhance Photosynthetic Productivity" 2012, *Appl Environ Microbiol* vol. 78, pp. 2660-2668.
Gong et al., ""Candidatus Sonnevornia yantaiensis", a member of candidate division OD1, as intracellular bacteria of the ciliated protist Paramecium bursaria (Ciliophora, Oligohymenophorea)" 2013, *Syst Appl Microbiol* vol. 37(2014), pp. 35-41.
Hoff and Stanke, "Predicting Genes in Single Genomes with AUGUSTUS" 2018, *Current Protoc Bioinformatics*, 62 pages.
Hoshina et al., "*Chlorella variabilis* and *Micractinium reisseri* sp. nov. (Chlorellaceae, Trebouxiophyceae): Redescription of the endosymbiotic green algae of Paramecium bursaria (Peniculia, Oligohymenophorea) in the 120th year" 2010, *Phycol Res* vol. 58, pp. 188-201.
Hu et al., "Microalgal triacylglycerols as feedstocks for biofuel production: perspectives and advances" 2008, *Plant J* vol. 54, pp. 621-639.
Jones Prather et al., "De novo biosynthetic pathways: rational design of microbial chemical factories" Curr Opin Biotechnol. Oct. 2008; 19(5):468-74.
Kimura, M., "A Simple Method for Estimating Evolutionary Rates of Base Substitutions Through Comparative Studies of Nucleotide Sequences" 1980, *J Mol Evol* vol. 16, pp. 111-120.
Kizer et al., "Application of Functional Genomics to Pathway Optimization for Increased Isoprenoid Production" Appl. Environ Microbiol. May 2008; 74(10):3229-41.
Knutson et al., "Effect of temperature control on green algae grown under continuous culture" 2018, *Algal Res* vol. 5, pp. 301-308.
Koren et al., Canu: scalable and accurate long-read assembly via adaptive k-mer weighting and repeat separation. *Genome Res* 27, 722-736 (2017).
Kumar et al., "MEGA X: Molecular Evolutionary Genetics Analysis across Computing Platforms" 2018, *Mol Biol Evol* vol. 35(6), pp. 1547-1549.
Letunic, I. and Bork, P., "Interactive Tree Of Life (iTOL) v4: recent updates and new developments" 2019, *Nucleic Acids Res* vol. 47, pp. W256-W259.
Mancipe et al., "Genomic analysis and characterization of Scenedesmus glucoliberatum PABB004: An unconventional sugar-secreting green alga" 2021, *Journal of Applied Microbiology* vol. 132 pp. 2004-2019.
Manni et al., "BUSCO: Assessing Genomic Data Quality and Beyond" 2021, *Current Protocols* 1:e323 vol. 1, pp. 1-41.

(Continued)

*Primary Examiner* — Christian L Fronda
(74) *Attorney, Agent, or Firm* — Mueting Raasch Group

(57) ABSTRACT

Culturing *S. glucoliberatum* PABB004 under conditions effective for the *S. glucoliberatum* PABB004 to secrete simple sugars into culture medium. In one or more embodiments, the conditions include a pH of 6.0 to 8.5. In some cases, the culture can include a second organism. A co-culture includes *S. glucoliberatum* PABB004 and a second organism, wherein the co-culture has a pH of 6.0 or greater. In one or more embodiments, the second organism is selected to produce a product of interest such as, for example, ethanol.

12 Claims, 6 Drawing Sheets

(56) References Cited

OTHER PUBLICATIONS

Ramachandra and Hebbale, "Bioethanol from macroalgae: Prospects and challengers" *Renew Sust Energ Rev*, Jan. 2020; 117, 109479.
Sanz Smachetti et al., "Sucrose-to-ethanol microalgae-based platform using seawater" Algal Res, Jan. 2020; 45, 101733.
Tillich et al., GeSeq—versatile and accurate annotation of organelle genomes. *Nucleic Acids Res* 45, W6-W11 (2017).
Xu et al., "OrthoVenn2: a web server for whole-genome comparison and annotation of orthologous clusters across multiple species" 2019, *Nucleic Acids Res* vol. 47, pp. W52-W58.

\* cited by examiner

ALGAL STRAIN AND METHODS FOR PRODUCING SIMPLE SUGARS

CROSS-REFERENCE TO RELATED APPLICATION

This is a divisional application of U.S. patent application Ser. No. 17/870,649, filed Jul. 21, 2022, which claims the benefit of U.S. Provisional Patent Application No. 63/224,948, filed Jul. 23, 2021, each of which is incorporated herein by reference in its entirety.

SUMMARY

This disclosure describes, in one aspect, a method that generally involves culturing S. glucoliberatum PABB004 under conditions effective for the S. glucoliberatum PABB004 to secrete simple sugars into culture medium.

In one or more embodiments, the conditions include a pH of 6.0 to 8.5.

In one or more embodiments, the S. glucoliberatum PABB004 is co-cultured with a second organism. In some cases, the second organism is a microbe selected to produce a product of interest. The microbe may be, for example, a bacterium a yeast, an archaeon, or a fungus. In one or more embodiments, the product of interest may be ethanol, a wax ester, a triacylglyceride, resorcinol, or a bioplastic. In one or more of these embodiments, the bioplastic can be polyhydroxybutyrate.

In another aspect, this disclosure describes a co-culture of S. glucoliberatum PABB004 and a second organism, wherein the co-culture has a pH of 6.0 or greater.

In one or more embodiments, the second organism is selected to produce a product of interest such as, for example, ethanol, a wax ester, a triacylglyceride, resorcinol, or a bioplastic.

In one or more embodiments, the co-culture can include the simple sugar produced by the S. glucoliberatum PABB004 that the second organism can metabolize in the process of producing the product of interest.

The above summary is not intended to describe each disclosed embodiment or every implementation of the present invention. The description that follows more particularly exemplifies illustrative embodiments. In several places throughout the application, guidance is provided through lists of examples, which examples can be used in various combinations. In each instance, the recited list serves only as a representative group and should not be interpreted as an exclusive list.

DETAILED DESCRIPTION OF ILLUSTRATIVE EMBODIMENTS

Figure 1:
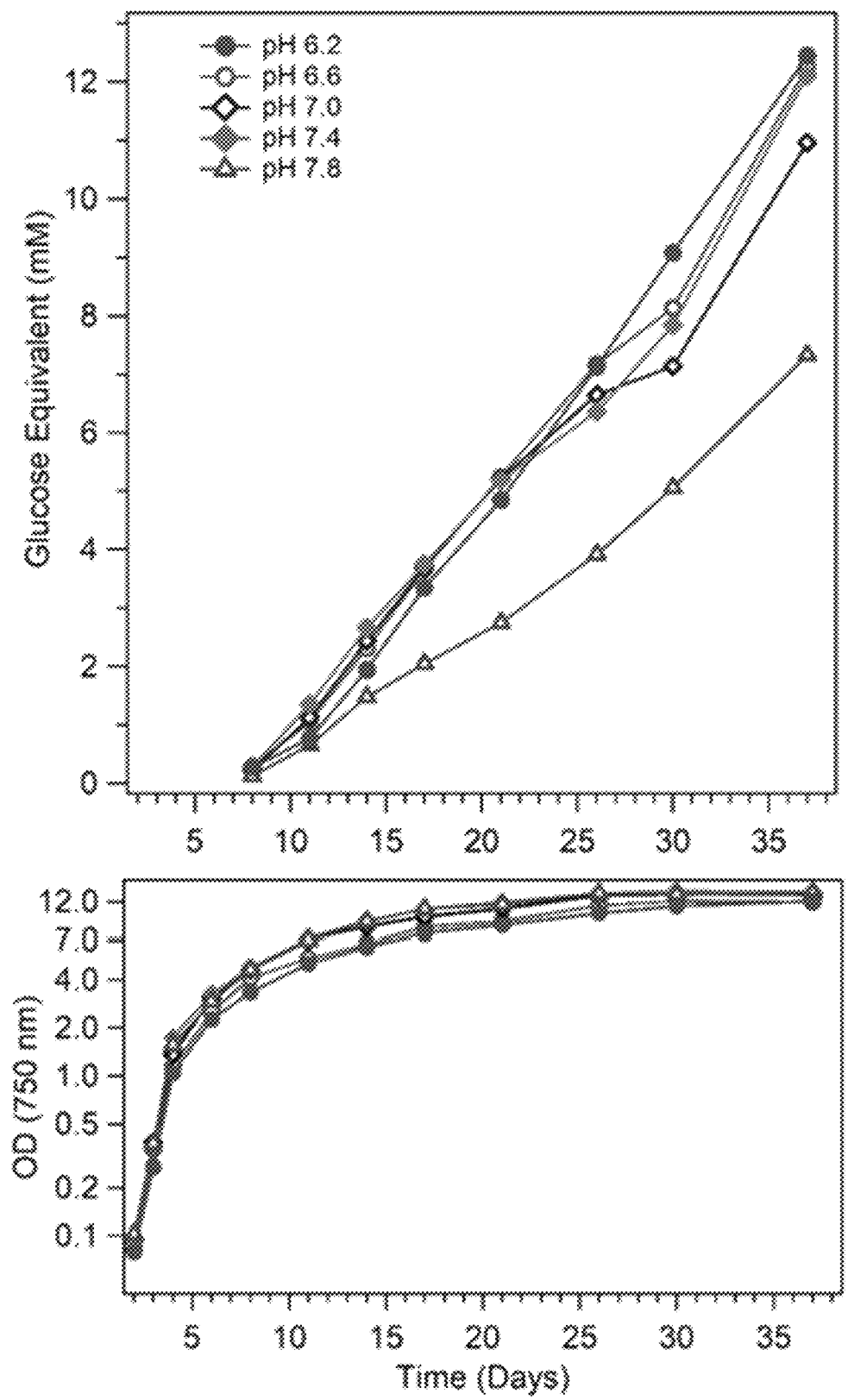
FIG. 1. Extracellular sugar accumulation versus growth rate for different pH values in Scenedesmus glucoliberatum PABB004. S. glucoliberatum PABB004 was cultured at various pH values for 37 days under standard laboratory conditions using a proton-balanced medium that minimized pH changes based on consumption of the nitrogen sources. Glucose equivalents are the combination of free glucose and glucose hydrolyzed from maltose through the action of α-glucosidase. Optical density measured at 750 nm is presented as a $Log_2$ plot.

This disclosure describes a microalgal strain that secretes simple sugars into the extracellular environment that are ready to use for co-culture schemes and fermentation processes. This disclosure also describes co-cultures of the microalgae strain with a second organism selected to produce a product of interest. This disclosure further describes methods of producing simple sugars using the microalgae strain and methods of co-culture of the microalgae strain with a microbe selected to biosynthesize a product of interest using the simple sugars secreted by the microalgae strain.

Biomass fermentation processes represent an alternative avenue to produce fuels and commodity chemicals with reduced environmental impacts. Currently, land crops (corn, sugarcane, sugar beets, etc.) are the main source of sugar-rich biomass for fermentations, but they require considerable cultivation time and post-harvest processing to extract and yield the monomeric sugars needed for downstream applications. Thus, feedstock costs represent a large portion of the total process costs, imposing minimum molar yields for commercial viability. The use of lignocellulosic biomass, electro-biotechnology approaches, and C1 feedstocks (CO, $CO_2$ and $CH_4$) have been proposed as potential solutions.

With this in mind, microalgae stand out for their ability to use C1 feedstocks, having a faster growth rate than land plants, and the availability of existing infrastructure for a variety of industrial applications.

Similar to what is found for land plants, sugar extraction from algae is generally based on biomass pretreatment followed by saccharification of cellulose and starch, but algae have simpler cell walls that facilitate this process. The potential use of algae as a source of hydrocarbons for bioprocessing has been reviewed (Hu et al., 2008, *Plant J* 54:621-639; Ramachandra and Hebbale, 2020, *Renew Sust Energ Rev* 117:18). Additionally, one can cultivate natural and modified sucrose-accumulating algae and cyanobacteria to increase sugar productivity (Ducat et al., 2012, *Appl Environ Microbiol* 78:2660-2668; Sanz Smachetti et al., 2020, *Algal Res* 45:9). Nonetheless, using natural sugar-secreting organisms as a source of readily recoverable sugars that do not require complex biomass processing has yet to be thoroughly explored.

Several species of sugar-secreting algae have been characterized from symbiotic relationships with Paramecium bursaria and *Hydra viridis*, mainly from the *Chlorella* and *Micractinium* genera, or in cnidarian-dinoflagellates associations found in coral reefs. When in the symbiotic state, algae cells are maintained within vacuoles inside the host species, where they release simple sugars such as, for example, maltose and lower amounts of glucose or glucose-6-phosphate. Sugar release from vacuoles may be regulated by decreasing the pH in the vacuolar compartments, and this relationship between acidic pH and sugar secretion has been observed in vitro. For example, *M. conductrix* can release as much as 5 g/L (14 mM) maltose at pH 5.7 in batch culture. As another example, *Chlorella* spp. such as *C.* sp. 3N813A can secrete maltose in the low µM range when cultured in media at pH 5. Unfortunately, the molecular mechanisms that enable sugar release remain unknown, partly due to the minimal genomic data available for algal species and a lack of transcriptomic profiles to correlate expression data with sugar-secreting phenotypes.

This disclosure describes a new sugar-secreting green microalga with differential characteristics compared to many previously reported sugar-accumulating *Chlorella* and *Micractinium* species. Linking phenotypic and genomic data, this disclosure provides information connecting the observation of desired phenotypes with the molecular basis of sugar secretion. Further, this disclosure increases the general pool of algal strains with desired capabilities for biotechnological applications.

Glucose and Maltose Secretion by *S. glucoliberatum* PABB004

To examine extracellular sugar production, *Scenedesmus glucoliberatum* PABB004 was cultured for several weeks at various pH levels ranging from 6.2 to 7.8 in nitrogen-limited medium and the supernatant was tested for the presence of simple sugars using an enzymatic approach. As shown in FIG. 1, the concentration of free extracellular maltose reaches the mM level. Sugar production commences once the culture enters the early stationary phase of growth, after approximately eight days of growth under the growth conditions of this experiment. The rate of sugar increase is relatively constant over time for each of the different pH values that were selected. Cell density did not differ substantially for different pH conditions, though lower pH cultures did experience a slightly longer lag phase. No fluctuations were found based on the time of day that samples were selected, indicating that the cultures do not consume substantial amounts of the extracellular sugar during the dark hours of culture. Contrary to expectations, the cultures were not especially prone to contamination, even with the substantial quantities of simple sugars that accumulated. This stability is attributed to the lack of other required nutrients, such as nitrogen, and the maintenance of somewhat aseptic techniques during culture and sampling.

Figure 6:
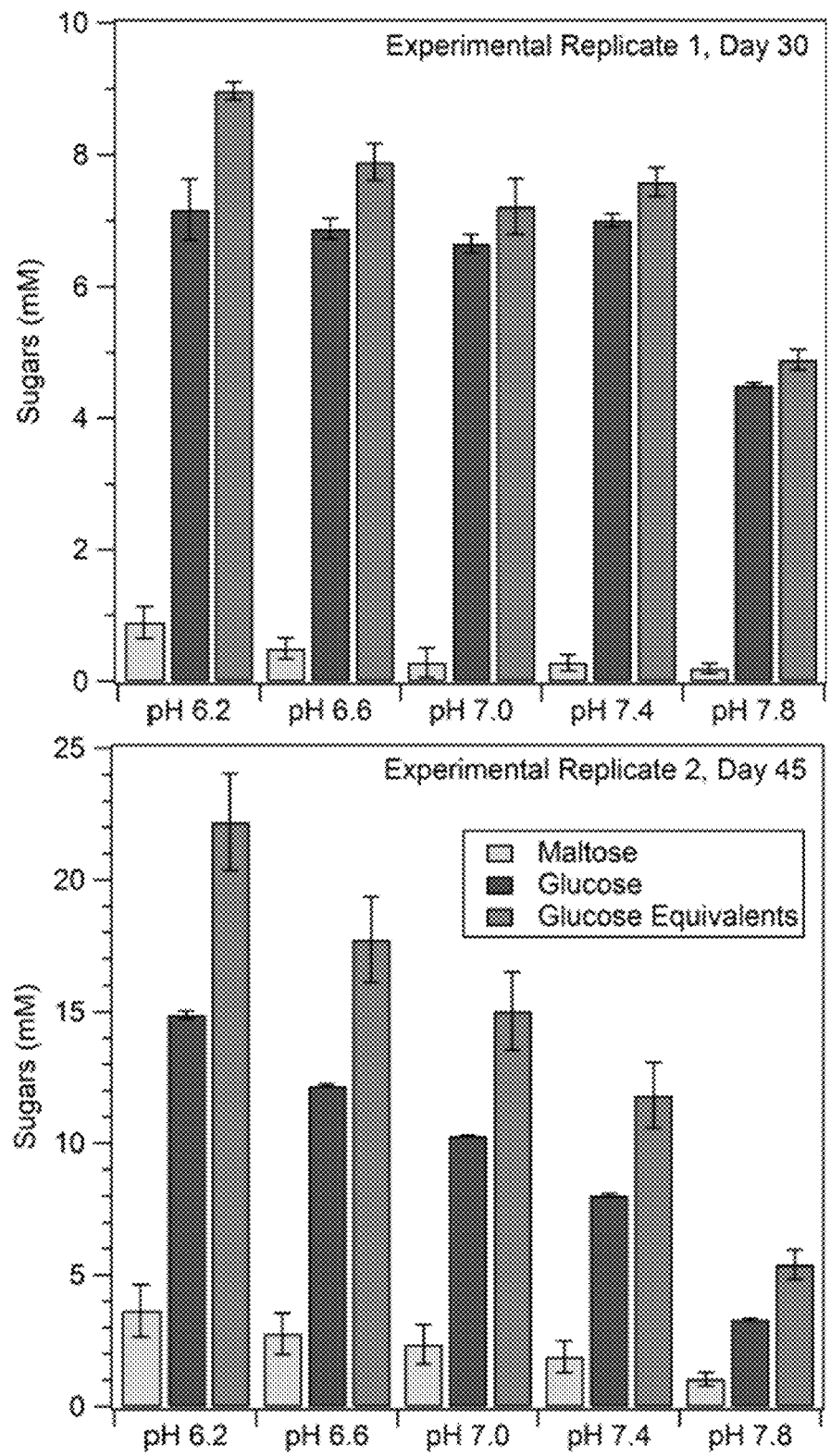
FIG. 6. S. glucoliberatum PABB004 sugar profiles from multiple experiments.

Extracellular glucose levels are consistently higher than maltose levels, reaching a maximum of 15 mM glucose versus 3.5 mM maltose at pH 6.2 in one independent experiment ran for up to 45 days (FIG. 6). In contrast to other green algae, glucose is the main secreted photosynthate in *S. glucoliberatum* PABB004 (FIG. 6).

The concentrations of both glucose and maltose in the media are partially dependent on medium acidity, though this dependence is more apparent during longer lengths of growth, with higher sugar levels arising at lower pH, and significant drops in sugar accumulation for pH 7.8. This relationship between acidity and sugar concentration appears to be more intense for the case of glucose—i.e., the reduction of extracellular glucose with increasing pH occurs faster than for the extracellular maltose at the same pH levels, suggesting a different response to pH changes in the mechanisms of glucose and maltose secretion.

*S. glucoliberatum* PABB004 Cell Morphology

Figure 2:
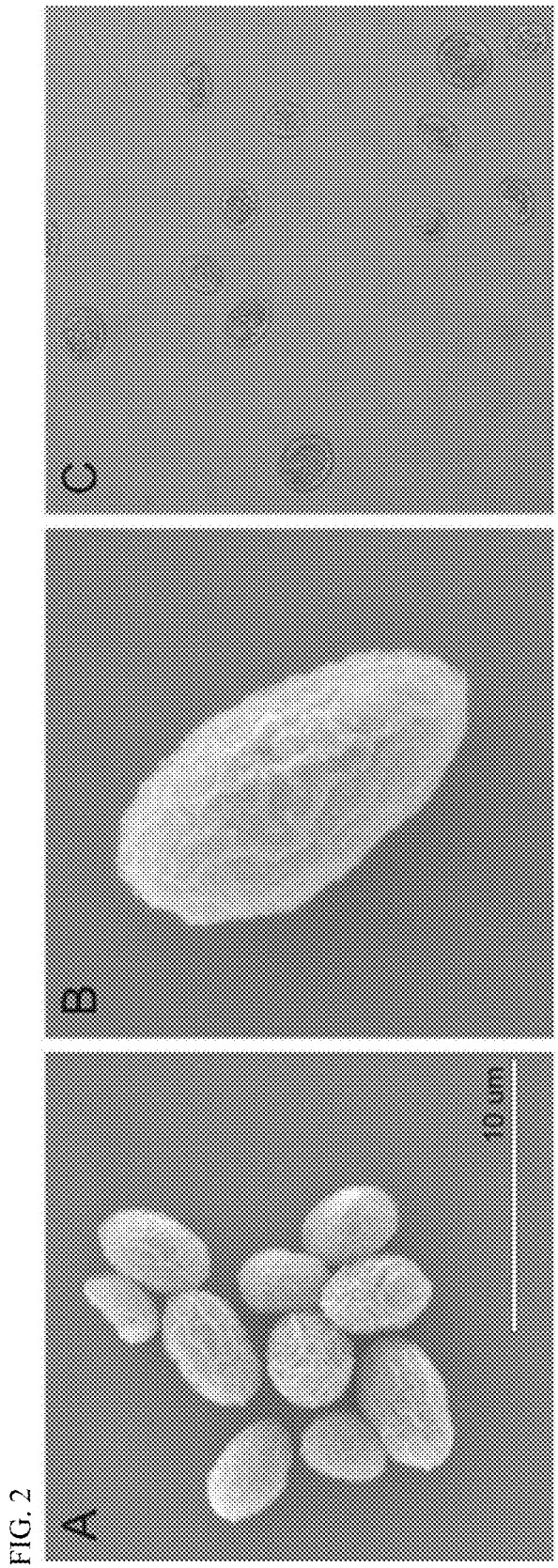
FIG. 2. Scenedesmus glucoliberatum PABB004 cell morphology. Cell suspensions were imaged using scanning electron microscopy and light microscopy. (A) Scanning electronic microscopy image. (B) Scanning electronic microscopy image. (C) Light microscopy image. The predominant distribution showed solitary cells and lack of outer structures such as flotation spines or flagella.

Vegetative cells of *S. glucoliberatum* PABB004 (FIG. 2) are ellipsoidal, approximately 4 m long and 2 m wide. Unlike other *Scenedesmus* spp., it does not present an elongated or sickle-like morphology nor form colonies in liquid culture. Instead, it lives predominantly as solitary cells. Outer structures such as flotation spines (common in *Scenedesmus* spp.) or flagella (common in *Chlamydomonas* spp.) were not observed. No differences in morphology were observed when growing at different pH values.

Genome Sequencing and Assembly

*S. glucoliberatum* PABB004 de novo draft genome hybrid assembly was performed using PacBio and Illumina sequencing data sets. The assembly was based on 854,693 PacBio reads with an average length of 8.2 kb and an average sequence coverage of 183×. The complete draft genome (39.97 Mb) was assembled in 80 contigs. From those, 77 belong to nuclear DNA, two to the chloroplast chromosome and the complete mitochondrion chromosome (Table 1).

TABLE 1

*S. glucoliberatum* PABB004 genome assembly and annotation statistics

| Assembly | |
|---|---|
| Total sequence length | 39.97 Mb |
| Sequencing depth | 183x |
| Number of contigs | 80 |
| Contig length range | [5.93 kb-4.85 Mb] |
| Contig average length | 499.66 kb |
| Contig median length | 206.87 kb |
| N50 | 1.29 Mb |
| L50 | 10 |
| PacBio reads used | 835,035 (97.7%) |
| Illumina reads mapped | 44,019,865 (98.4%) |
| BUSCO genome scores | C = 95.0% |
| | [S = 93.7%, D = 1.3%], |
| | F = 1.5%, M = 3.5% |
| GC content | 78.38% |
| Annotation | |
| CDS count | 6947 |
| Models with homology support (SwissProt database) | 3062 (44%) |
| Models with homology support (KEGG database) | 3105 (45%) |

Half of the assembled genome is contained in 10 contigs (L50), all of those longer than 1.3 Mb (N50). From the 1,519

Benchmarking Universal Single-Copy Orthologs (BUSCOs; Manni et al., 2021, *Current Protocols* 1:e323) in the Chlorophyta dataset used to assess the assembly completeness, 93.7% were found as single copy, 1.3% were duplicated, 1.5% were fragmented and 3.5% missing. These percentages show that the assembly coverage and contiguity are of good quality and good representatives of the genetic background for the following comparisons.

Genomic Features of *S. glucoliberatum* PABB004

The *S. glucoliberatum* PABB004 nuclear DNA contains two contigs with telomeric repeats on both ends, indicating full chromosomes (contigs 1 and 6) and 34 others with telomeric repeats on one end only. This suggests the existence of at least 19 nuclear chromosomes (Table 2).

the 191.3 kb is represented in two contigs of 154.4 kb and 36.9 kb. The shortest contig is highly similar to the longest (99.95% nucleotide identity on the reverse complementary sequence, 100% coverage) and it is likely the inverted repeat segment commonly found in plastid genomes. The plastid GC content is similar to the reference green alga in Table 2 and its CDS density, 0.31 genes per kb, is similar to *C. reinhardtii* (0.34 genes per kb).

The mitochondrial genome was completely assembled in one circular contig with no gaps. The chromosome length was 26.6 kb with a GC content of 36.8%, 15 CDSs and a gene density of 0.56 genes/kb. These values are within the length and GC content range reported from other green algal genomes (Table 2). Moreover, the closely related *Tetrades-*

TABLE 2

Genomic features of *S. glucoliberatum* PABB004 and selected algae

|  | *S. glucoliberatum* PABB004 | *M. neglectum* [†] | *C. reinhardtii* [‡] | *C. variabilis* [§] |
|---|---|---|---|---|
| Nuclear DNA |  |  |  |  |
| Total sequence length (Mb) | 39.8 | 69.5 | 111.1 | 46.2 |
| Chromosomes | >=19 | — | 17 | 12 |
| GC content (%) | 78.6 | 64.2 | 61.9 | 65.5 |
| CDS count | 6855 | 16717 | 17700 | 9780 |
| Plastid DNA |  |  |  |  |
| Total sequence length (kb) | 191.3 | 140 | 203.8 | 124.7 |
| GC content (%) | 32.1 | 32.4 | 34.5 | 33.9 |
| CDS count | 76 | 4 | 69 | 114 |
| Mitochondrion chromosome |  |  |  |  |
| Total sequence length (kb) | 26.6 | 90 | 15.8 | 78.5 |
| GC content (%) | 36.8 | 45.5 | 45.2 | 28.3 |
| CDS count | 15 | 17 | 8 | 62 |

Genome assembly accessions
[†] GCA_000611645.1,
[‡] ABCN00000000.2 and
[§] GCA_000147415.1

Assembly results did not show any evidence of polyploidy. Total nuclear DNA length is 39.8 Mb, considerably smaller than *Monoraphidium neglectum* (69.5 Mb, accession Uniprot: UP000054498, NCBI: GCA_000611645.1), which was the closest algae in taxonomic terms found with its plastid, mitochondrial, and nuclear genomes annotated. *S. glucoliberatum* PABB004 has the third smallest genome and the highest GC content (78%, Table 2) within the Sphaeropleales genomes in the current NCBI database.

The gene prediction approach resulted in the annotation of 6947 CDSs. Prediction quality was evaluated with BUSCO (Manni et al., 2021, *Current Protocols* 1:e323) on protein mode and the chlorophyta_odb10 dataset, which contains 1519 orthologous genes. Results show a prediction outcome with 91.1% complete genes (88.2% found as single copy and 2.9% duplicated), 0.3% genes fragmented and 8.6% missing, which is comparable to the quality of the proteomes reported in the SwissProt database.

There were 6872 CDSs in the nuclear contigs, accounting for a gene density of 172.7 genes per Mb, which is slightly higher than *C. reinhardtii* (159 genes per Mb) and lower than *M. neglectum* and *C. variabilis* (with 240 and 212 genes per Mb, respectively). This value for the *S. glucoliberatum* PABB004 genome only represents protein coding sequences—i.e., non-coding sequences, tRNA genes, and rRNA genes were not included in the gene counts.

The chloroplast chromosome could not be completely closed with the assembly approach described above. Instead,

*mus obliquus* mitochondrion has 43 kb, 36.2% GC, 20 CDSs, and 0.47 genes/kb (NCBI bioproject accession PRJNA11896), which shows that the *S. glucoliberatum* PABB004 mitochondrion is quite similar in GC content but slightly more compact, i.e., with only 62% of the length it contains 75% of the total CDSs in *T. obliquus*. Additionally, the relationship between these two species is supported by the use of the same mitochondrial genetic code, which differs from the standard code in the codons TCA being translated to stop instead of Ser and TAG to Leu instead of stop.

Taxonomic Analysis of *S. glucoliberatum* PABB004

The taxonomic classification of *S. glucoliberatum* PABB004 was performed through a phylogenetic approach using the conserved SSU rRNA and variable internal transcribed spacer (ITS) regions and a phylogenomic comparison based on the average nucleotide identity between the *S. glucoliberatum* PABB004 transcriptome and related green algae.

An initial BLASTn search of the *S. glucoliberatum* PABB004 genomic region containing the SSU rRNA, ITS 1, and ITS 2 revealed that it belongs to the Chlorophyceae clade within the green algae. This result was unexpected since *P. bursaria* endophytes are usually found within the *Chlorella* and *Micractinium* genera, which belong to the Trebouxiophyceae clade. Hence, a broader analysis including a wide range of Chlorophyceae organisms was performed. The resulting phylogenetic tree (FIG. 3) supports the grouping of S. glucoliberatum PABB004 within the Chlorophyceae as part of the Sphaeropleales clade. Furthermore, the bootstrap consensus shows that in 96 out of 100 replicates S. glucoliberatum PABB004 is placed with the Scenedesmaceae family. Using this approach, the exact genus and species of the isolate could not be determined.

Figure 4:
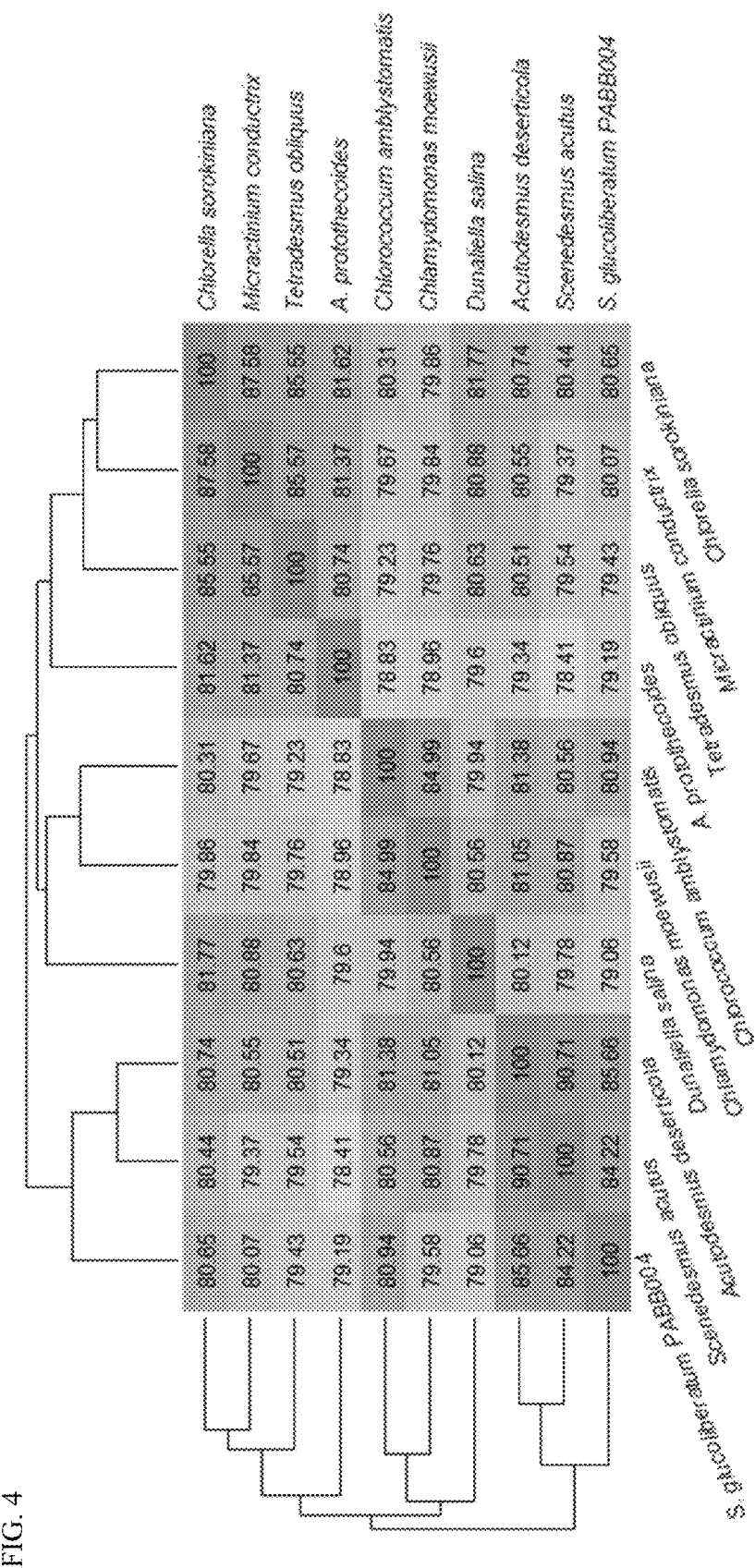
FIG. 4. S. glucoliberatum PABB004 phylogenomic relationships. Average Nucleotide Identity (ANI) values were calculated based on BLAST identity scores generated by pairwise comparisons between organisms. Sequences were taken from 98 clusters of orthologous transcribed sequences among all taxa analyzed. Organisms were then classified based on their ANI scores. S. glucoliberatum PABB004 clustered together with other Sphaeropleales (S. acutus and A. deserticola), other Chlorophyceae alga from different clades and Chlorellales were grouped in separate branches.

The S. glucoliberatum PABB004 transcriptome was compared with transcriptomes from other green algae. All transcripts were clustered based on sequence similarity and the average nucleotide identity of orthologous sequences was calculated between pairs of organisms. As shown in FIG. 4, S. glucoliberatum PABB004 is grouped with two other Scenedesmaceae algae (S. acutus and Acutodesmus deserticola), confirming the results of the previous phylogenetic analysis while the other Chlorophyceae and Trebouxiophyceae were grouped in different clades.

Since both methods support the placement of the isolate within the Scenedesmaceae family and its closest organisms belong to the Scenedesmus genus based on the SSU rRNA data, the new isolate was named Scenedesmus glucoliberatum PABB004.

Proteomic Comparisons Among S. glucoliberatum PABB004 and Selected Green Algae

Understanding the genetic mechanisms in green alga that allow the secretion of simple sugars to the extracellular environment could enable the manipulation of such pathways for their use in biotechnological applications. Therefore, the set of predicted CDSs and respective proteins contained in the S. glucoliberatum PABB004 genome was analyzed through a sequence similarity and clustering approach. The goal of this search was defining a subset of sequences that are present only in algae with sugar secreting phenotypes (M. conductrix and S. glucoliberatum PABB004) and absent from their non-sugar secreting controls. C. reinhardtii and C. sorokiniana were chosen as controls for S. glucoliberatum PABB004 and M. conductrix due to their evolutionary relatedness and apparent lack of extracellular sugar secretion phenotypes.

The curated proteomes from M. conductrix, C. sorokiniana and C. reinhardtii were obtained from the Uniprot-Swissprot database, compared with S. glucoliberatum PABB004 and clustered based on sequence similarity (Table 3).

TABLE 3

Proteome clustering results among selected green algae

| Source | Total Proteins | Clustered proteins† | Singletons‡ |
|---|---|---|---|
| Proteomes | | | |
| C. reinhardtii (UP000006906) | 18829 | 12560 (7049) | 6269 |
| C. sorokiniana (UP000239899) | 9482 | 7527 (6710) | 1955 |
| M. conductrix (UP000239649) | 9122 | 7567 (6616) | 1555 |
| S. glucoliberatum PABB004 (this study) | 6947 | 5354 (4563) | 1593 |
| Selected intersection sets | | | |
| M. conductrix ∩ C. sorokiniana | — | (6150) | — |
| S. glucoliberatum PABB004 ∩ C. reinhardtii | — | (4258) | — |
| Core | 14411 | (3098) | — |
| S. glucoliberatum PABB004 ∩ M. conductrix only | 52 | (23) | — |
| S. glucoliberatum PABB004 only | 269 | (97) | — |

†Values in parenthesis represent the number of protein clusters
‡Protein sequences not classified within any homology group From the 18829 proteins in the C. reinhardtii proteome, 12560 were classified in 7049 homologous groups ("clusters") and the remaining 6269 did not show homology relationships to other sequences ("singletons"). Similarly, the C. sorokiniana proteome with 9482 proteins was classified in 6710 clusters with 7527 proteins and 1955 singletons; the 9122 proteins of M. conductrix were organized in 6616 clusters with 7567 proteins and 1555 singletons and the 6947 proteins from S. glucoliberatum PABB004 were classified as 5354 proteins grouped in 4563 clusters and 1593 singletons.

Figure 5:
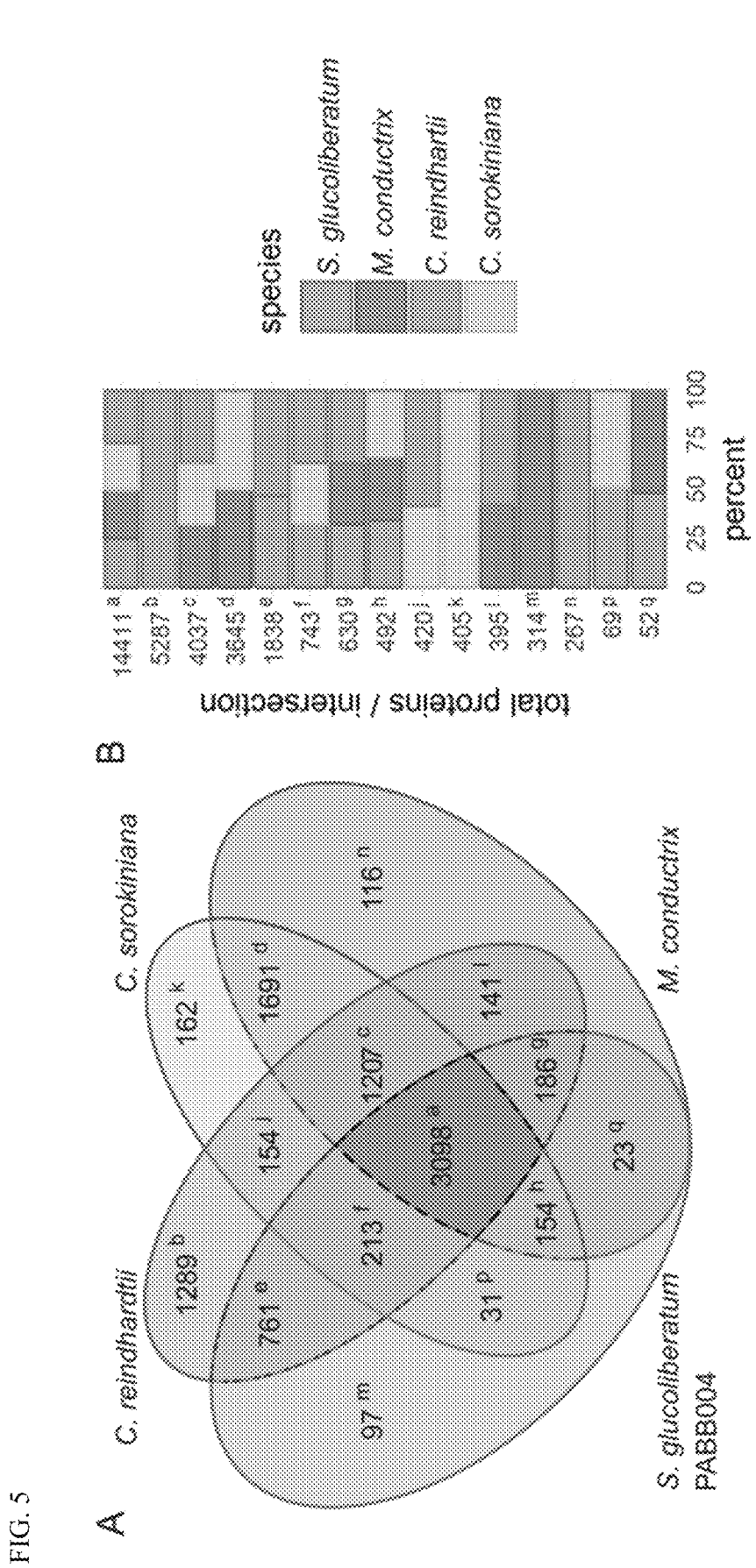
FIG. 5. Proteomic comparisons among sugar-secreting and non-secreting algae. The Uniprot-Swisspro proteomes of C. sorokiniana, M. conductrix, and C. reindhardtii were compared to S. glucoliberatum PABB004 predicted proteome using OrthoVenn2 with a blastp cutoff of $1\times10^{-10}$. The proteins were clustered in homologous groups based on sequence similarity. (A) Venn diagram depicting the number of protein clusters shared by or unique to the four green algae. The number of clusters is shown instead of number of individual proteins due to the different copy number of some homologous sequences among species. (B) Protein count in each intersection in (A) and the percent contribution of each species. As a reference, each intersection is labeled with a letter superscript in (A) and (B).

As shown in Table 3 and FIG. 5, most of the proteins analyzed belong to a core subset of 3098 clusters that are shared among all algae (labeled with the superscript "a" at the center of FIG. 5), which aligns with all organisms belonging to the Chlorophyta clade and hence must share a high percentage of their genomic resources. This core subset contains 68% of all S. glucoliberatum PABB004 clusters, 44% of C. reinhardtii, 46% of C. sorokiniana and 47% of M. conductrix. Proteins in this subset have basic functions that range from photosystem assembly to transcription and ribosomal activity, metabolism, and transport processes.

The overall level of homology among proteomes tends to correlate with the evolutionary history of the algae analyzed. For example, the intersection between M. conductrix and C. sorokiniana (M. conductrix∩C. sorokiniana in Table 3 and superscripts a, c, d, and h in FIG. 5) contains the highest number of shared clusters (6150), which represent 93% and 92% of each organism's total count. This result aligns with both organisms being closely related and having similar sized proteomes.

For S. glucoliberatum PABB004, 93% of its clusters are shared with C. reindhardtii (S. glucoliberatum PABB004∩C. reinhardtii in Table 3 and superscripts a, e, f, and g in FIG. 5). Without including the core set shared by all algae, the overlap between S. glucoliberatum PABB004 and C. reindhardtii accounts for 26% of all its clusters, which is more than three times greater than its overlap with C. sorokiniana or M. conductrix (about 8% each). This supports the classification of S. glucoliberatum PABB004 in the Chlorophyceae clade.

Moreover, if the sugar-secreting phenotype is related to the existence of unique genes that enable the process, then such genes are likely contained in the subset common to S. glucoliberatum PABB004 and M. conductrix and absent from the other two algae ((S. glucoliberatum PABB004∩M. conductrix)⊂(C. sorokiniana∪C. reinhardtii), superscript q). Since both sugar-secreting algae share a large percentage of their proteome with non-sugar-secretors (>90%), a comparison between all proteomes, followed by the selection of clusters that exist exclusively in the sugar-secreting species results in a reduced subset of proteins. This subset (S. glucoliberatum PABB004∩M. conductrix only) contains 23 clusters with 27 proteins from M. conductrix and 25 from S. glucoliberatum PABB004. The 25 S. glucoliberatum PABB004 proteins in this subset were further analyzed through BLASTp and InterProScan searches, looking for evidence of a unique sugar transporter. Preliminary results failed to identify such a transporter. Nonetheless, a deeper examination of the shared sequences between both algae and their transcription profiles would be necessary to further understand their potential role in the maltose secretion process. Thus, a pool of protein sequences unique to S. glucoliberatum PABB004 (superscript m in FIG. 5) that might be involved in the unconventional sugar secretion characteristics of this alga (i.e., the secretion of glucose as the main photosynthate) was generated.

Metabolic Traits of S. glucoliberatum PABB004 Inferred from its Genomic Data

The metabolic characteristics of S. glucoliberatum PABB004 were examined through the Kyoto Encyclopedia of Genes and Genomes (KEGG) annotation and their Mapper tool. A total of 3105 proteins (45% of the proteome) were assigned a KEGG orthology accession, mapping to 380 pathways and were classified in 45 different BRITE functional hierarchies. Due to the role of some proteins in various pathways or cell processes, the total count of hits for all categories is much greater than the actual protein count.

KEGG found 92 orthologs for carbon metabolism pathways (ko01200) in S. glucoliberatum PABB004, including 26 for glycolysis/gluconeogenesis (ko00010), 21 for the TCA cycle (ko00020), 16 for the pentose phosphate pathway (ko00030), and 22 in carbon fixation (ko00710). All these basic pathways had a complete representation in S. glucoliberatum PABB004 predicted proteome. KEGG also found 23 orthologs for fatty acid metabolism (ko01212) that generate an uninterrupted pathway from acetyl-CoA to stearoyl-CoA. The pathway connecting to longer-chain compounds has several missing genes. There were also 88 orthologs for biosynthesis of amino acids (ko01230), which completed an uninterrupted path to produce all amino acids except histidine, tryptophan, methionine, arginine, and proline. This could be due to an incomplete annotation process whether at the structural or functional steps.

Additionally, C. reinhardtii, and C. variabilis were used as reference organisms to contrast the distribution of BRITE hierarchies. The most common hierarchies for S. glucoliberatum PABB004 are shown in Table 4.

parisons between the three algae were performed with a Wilcoxon-rank test ($H_0$: the pair of organisms compared have the same distribution of hits among BRITE categories, $H_a$: they have a different distribution of hits). The results confirmed the alternative hypothesis for S. glucoliberatum PABB004 (p-values $2.9 \times 10^{-5}$ for S. glucoliberatum PABB004 versus C. reinhardtii and $3.8 \times 10^{-5}$ for S. glucoliberatum PABB004 vs. C. variabilis), while there was no evidence of a difference between C. reinhardtii and C. variabilis (p-value 0.9).

This observation means that S. glucoliberatum PABB004 has a different relative content of proteins within its proteome when compared to the other two organisms. In detail, the hierarchies "Ribosome biogenesis" and "Ubiquitin system" and "Messenger RNA biogenesis" seem to have a higher relative content in S. glucoliberatum PABB004 than in C. variabilis. Since the raw number of proteins in those categories among the three organisms is similar, S. glucoliberatum PABB004 seems to have a higher representation due to its reduced proteome size. This implies that proteins from other hierarchies have been lost through evolution or were never present in S. glucoliberatum PABB004.

This disclosure therefore describes the microalga Scenedesmus glucoliberatum PABB004. The genome sequence of S. glucoliberatum PABB004 expands the limited number of assembled green algae genomes, and offers a stark contrast to other sequenced strains of Scenedesmus. S. glucoliberatum PABB004 is of particular interest for fermentative processes or in co-culture schemes with other organisms due to its advantageous sugar-secretion pheno-

TABLE 4

Selected BRITE functional hierarchies for S. glucoliberatum PABB004 proteins and other green algae[†]

| Functional category | S. glucoliberatum PABB004 | C. reinhardtii | C. variabilis |
|---|---|---|---|
| ko01000 Enzymes | 1254 (I) | 1903 (I) | 1919 (I) |
| ko03036 Chromosome and associated proteins | 260 (II) | 628 (II) | 407 (II) |
| ko04131 Membrane trafficking [‡] | 212 (III) | 357 (IV) | 344 (III) |
| ko03009 Ribosome biogenesis [‡ §] | 156 (IV) | 189 (X) | 202 (IX) |
| ko04121 Ubiquitin system [‡ §] | 139 (V) | 177 (XII) | 166 (XIII) |
| ko03041 Spliceosome | 135 (VI) | 285 (V) | 299 (V) |
| ko03400 DNA repair and recombination proteins [‡] | 129 (VII) | 198 (IX) | 223 (VIII) |
| ko04147 Exosome | 127 (VIII) | 426 (III) | 320 (IV) |
| ko03019 Messenger RNA biogenesis [§] | 125 (IX) | 202 (VIII) | 186 (XII) |
| ko03029 Mitochondrial biogenesis [‡] | 121 (X) | 179 (XI) | 195 (X) |
| ko02000 Transporters | 117 (XI) | 247 (VI) | 240 (VI) |
| ko03011 Ribosome | 102 (XII) | 243 (VII) | 237 (VII) |
| ko01002 Peptidases and inhibitors [‡ §] | 100 (XIII) | 129 (XIV) | 128 (XIV or XV) |
| ko03016 Transfer RNA biogenesis | 89 (XIV) | 165 (XIII) | 188 (XI) |
| ko03021 Transcription machinery [‡] | 74 (XV) | 108 (XVII) | 128 (XIV or XV) |
| ko03110 Chaperones and folding catalysts | 72 (XVI) | 114 (XV) | 103 (XVI) |
| ko03032 DNA replication proteins [‡] | 66 (XVII) | 78 (XIX) | 84 (XVII or XVIII) |
| ko01009 Protein phosphatases and associated proteins | 58 (XVIII) | 97 (XVIII) | 84 (XVII or XVIII) |
| ko04812 Cytoskeleton proteins [§] | 56 (XIX) | 109 (XVI) | 54 (XX) |
| ko00194 Photosynthesis proteins [‡ §] | 48 (XX) | 60 (XXI) | 49 (XXI or XXII) |
| ko03051 Proteasome | 35 (XXI or XXII) | 49 (XXII) | 49 (XXI or XXII) |
| ko01003 Glycosyltransferases | 35 (XXI or XXII) | 65 (XX) | 76 (XIX) |
| ko02044 Secretion system | 17 (XXIII) | 27 (XXIII) | 28 (XXIII) |

[†]Number of hits per hierarchy, sequences may have hits in various categories. The ranked order of hierarchies for each alga is given in parenthesis.
[‡] Hierarchy with higher rank in S. glucoliberatum PABB004 than in C. reinhardtii
[§] Hierarchy with higher rank in S. glucoliberatum PABB004 than in C. variabilis The three analyzed algae have a different number of proteins classified in each category, which is expected as each have different sized proteomes. Therefore, the comparison of ranks was favored over the raw protein count. Paired comtype, even at physiological pH ranges. The evolutionary history, inferred from its genomic traits, expands current understanding of algal mutualistic relationships involving photosynthate exchanges.

Sugar-Secreting Phenotype

*S. glucoliberatum* PABB004 secretes ready-to-use fermentable sugars (glucose and maltose) to the culture media, demonstrating an advantage over other feedstock sources that require biomass pretreatment and saccharification steps. The highest carbohydrate levels recorded in batch cultures were 2.7 g/L of free glucose and 1.2 g/L of maltose at pH 6.2 (FIG. 6).

Glucose levels revealed here are higher than what has been reported previously for *Micractinium* and *Chlorella* spp (Arriola et al., 2018, *Plant J* 93:566-586; Brechignac and Schiller, 1992, *Adv Space Res* 12(5):33-36 (Hoff and Stanke, 2018, *Current Protoc Bioinformatics*; Dorling et al., 1997, *Eur J Phycol* 32:19-24). Furthermore, sugar concentration in the media also shows an inverse trend with pH. In the case of *S. glucoliberatum* PABB004, the pH range in which the secretion takes place at significant sugar concentrations is broader than that from *Micractinium* and *Chlorella* spp. This isolate secreted considerable levels of sugars at all pH levels tested (pH 6.2, 6.6, 7.0, 7.4, and 7.8; FIG. 11) while *M. conductrix* and *Chlorella* sp. 3N813A secreted negligible sugars at pH levels above 7.6 and 7.0, respectively (Arriola et al., 2018, *Plant J* 93:566-586; Dorling et al., 1997, *Eur J Phycol* 32:19-24). This trait represents a potential advantage in industrial applications over other sugar-secreting algae since it offers a greater process flexibility and resilience. Thus, *S. glucoliberatum* PABB004 provides an algal strain that produces fermentable carbon sources for biotechnological applications and in co-culture schemes investigating nutrient exchange (Barney et al., 2015, *Appl Environ Microbiol* 81(13):4316-4328).

Phylogenetic Lineage

Figure 3:
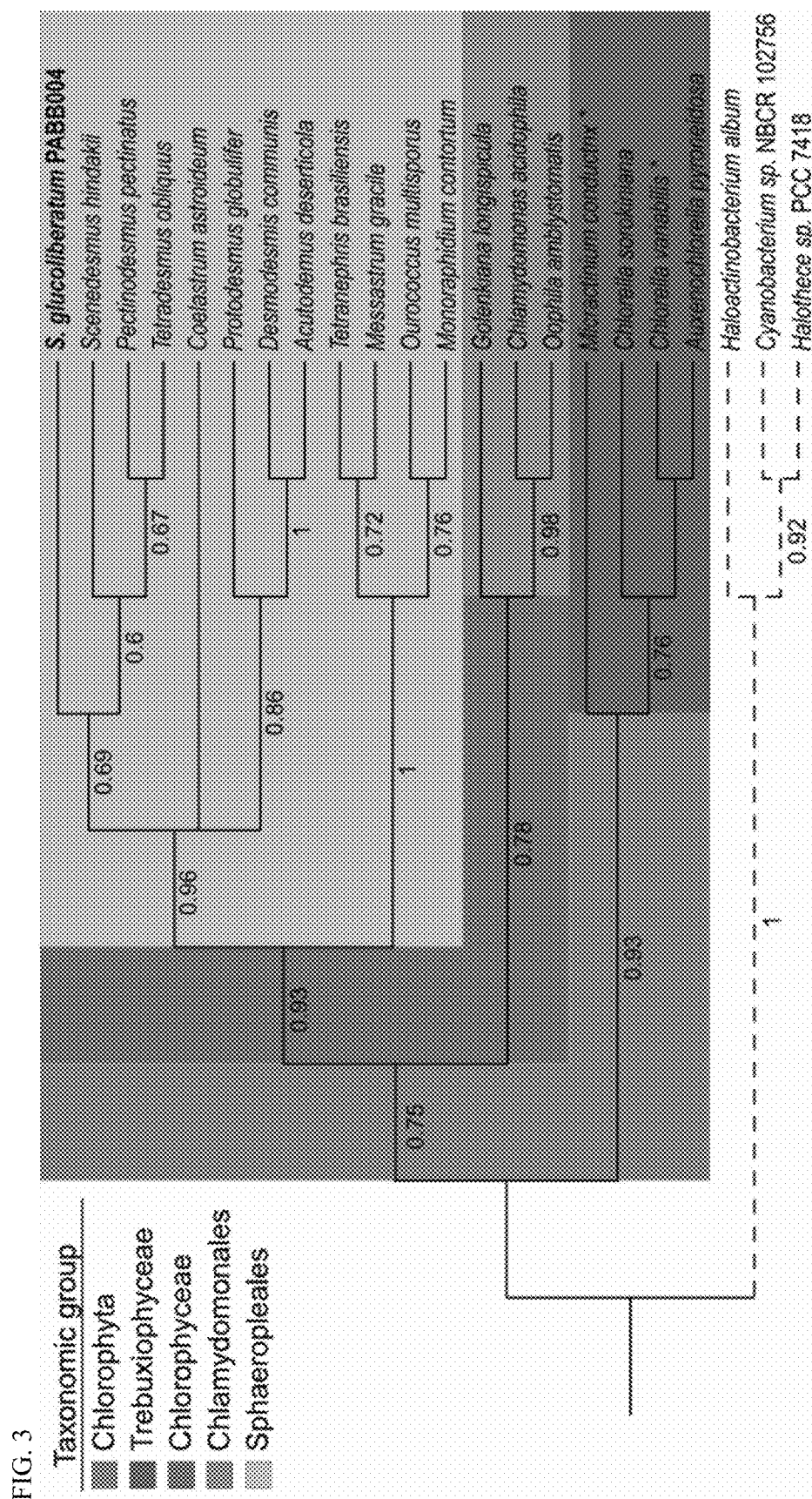
FIG. 3. Scenedesmus glucoliberatum PABB004 phylogenetic classification. Evolutionary history of S. glucoliberatum PABB004 was inferred using the Maximum Likelihood method and Kimura 2-parameter model applied to calculate the evolutionary distances among 22 SSU rRNA sequences. The phylogenetic tree was generated with a bootstrap consensus from 100 replicates. The frequency of replicate trees in which the associated taxa clustered together in the bootstrap test are shown next to the branches. Taxonomic clades are coded by shading and known P. bursaria endosymbionts are marked with an asterisk. Dashed lines correspond to the outlier sequences branch.

The evolutionary history of *S. glucoliberatum* PABB004 was investigated using sequence similarity and likelihood-based inference approaches. First, its SSU rRNA gene and ITS regions were compared, as phylogenetic markers, with a broad range of green algae homologs (FIG. 3). The 5' segment of the SSU rRNA gene contains a highly variable region that does not align well with any sequence tested, but the rest of the sequence is highly similar to those from species from the Sphaeropleales and Scenedesmaceae clades. Moreover, the average nucleotide identity between expressed transcripts from various Chlorophyceae and Trebouxophiceae algae support this strain designation (FIG. 4 and FIG. 5).

The results show that *S. glucoliberatum* PABB004 does not belong to the *Micractinium* or *Chlorella* genera, known for their close mutualistic relationships with *P. bursaria* involving maltose secretion and exchange. Instead, it is placed on the Chlorophyceae-Sphaeropleales-Scenedesmaceae branch of the tree of life. While the potential to maintain certain *Scenedesmus* strains in *P. bursaria* has been reported, there are no reports of Scenedesmaceae algae isolated from *P. bursaria* and shown to release extracellular simple sugars, even in studies testing green algal symbionts from distant geographical locations. It is possible that prior reports have mistakenly classified prior *Scenedesmus* species as *Chlorella* based solely on visual inspections and morphology. Hence, *S. glucoliberatum* PABB004 presents an interesting opportunity to expand understanding of these aspects of algal physiology and plant evolution.

*S. glucoliberatum* PABB004 was isolated from ruptured cells of *P. bursaria* isolated from a small selection of natural environments surrounding Minneapolis, Minnesota. This approach was used to screen for additional wild strains of sugar-secreting algae, and yielded several strains of algae outside of the *Micractinium* and *Chlorella* genera with initial sugar-releasing phenotypes. This screen was by no means exhaustive, and represents only a minimal effort directed at expanding the range and versatility of sugar release in green algae. While these simple screens were successful in uncovering new examples of the sugar-releasing phenotype, studies to determine if these strains can be successfully added back to algal-deficient *P. bursaria* to rescue the symbiotic relationship were beyond the scope of this study. However, the success of this simple screen illustrates the potential of such studies to identify new strains of sugar-releasing algae from natural environments. This approach could be much more successful than broad screens of random algal strains, as the *P. bursaria* host strain pre-selects for the sugar-release phenotype, or simply digests that algal cell in the absence of sugar-release.

A general hallmark of the *Scenedesmus* genera is the multicellular colonial lifestyle where they are often found in coenobia of four or eight cells. While there are also examples of unicellular *Scenedesmus* strains, this colonial cell morphological feature is often used to classify these algae following an initial visual inspection. Symbiotic sugar-releasing algae found in *P. bursaria* are generally housed in what is referred to as a perialgal vacuole, which may not be amenable to algae that employ colonial lifestyles.

*S. glucoliberatum* PABB004 Genomic Features and Resources

Another interesting feature of this isolate is its compact genome with several differential characteristics compared to other green algae in its clade. *S. glucoliberatum* PABB004 has the third smallest genome and the highest GC content within the Sphaeropleales genomes currently published in the GenBank database. Its predicted proteome contains only about 7000 proteins, merely 1.5 times the protein count of many strains of *Escherichia coli*.

Such a small genome size and low protein count in the light of the proteome comparison performed here (FIG. 5 and Table 4) suggests a possible reduction in the *S. glucoliberatum* PABB004 genome to contain mostly essential and highly conserved genes. In fact, 68% of its protein families are clustered within a core set shared by other green algae (*C. reinhardtii*, *C. sorokiniana* and *M. conductrix*), while this same set only contains on average 46% of the total clusters in the other species (Table 3 and FIG. 5A). This trait is commonly found in symbiont organisms and is believed to have played a key role in the evolution of organelle structures, as a feature often attributed to endosymbiotic organisms is a reductive evolution related to prolonged growth in a stable and specific ecological niche. In this context, the genome of *S. glucoliberatum* PABB004 has a smaller genome versus other reported strains of *Scenedesmus*. However, it is also uncertain the length of time that any specific alga has been in close association with strains of *P. bursaria*, which is especially true in this case. Many endosymbionts obtained from *P. bursaria* are capable of independent growth outside of the strain, so the question of how stable and prolonged the mutualistic symbiotic relationships are between green algae and *P. bursaria* is still very much outstanding.

Finally, proteome comparisons identified two sequence sets that could be used to direct further research on the molecular mechanisms of sugar secretion by green algae. With these, and a further collection of additional strains and characterization, one may identify the common directives for simple sugar secretion and those unique to the *S. glucoliberatum* PABB004 glucose secretion phenotype.

This disclosure therefore describes a method for producing simple sugars in culture. In one or more embodiments, the simple sugar can include glucose or maltose. Generally, the method includes culturing S. glucoliberatum PABB004 under conditions effective for the S. glucoliberatum PABB004 to secrete simple sugars into culture medium. In one or more embodiments, the culture conditions include providing $CO_2$ as a carbon source for use by S. glucoliberatum PABB004 to produce the simple sugar. In one or more of these embodiments, $CO_2$ can be the sole carbon source for use by S. glucoliberatum PABB004 to produce the simple sugar. Generally, the culture conditions include a pH of 6.0 to 8.5. Other methods for producing simple sugars by algae in culture involve culture conditions in which the pH is 6.0 or lower. In contrast, S. glucoliberatum PABB004 can produce simple sugars in culture where the culture medium has a pH of 6.0 and higher, conditions that are more amenable to co-culture of S. glucoliberatum PABB004 with a microbe (e.g., a bacterium, a yeast, an archaeon, a fungus, etc.) that are selected to feed on the simple sugars and produce one or more products of interest—e.g., ethanol, a wax ester, a triacylglyceride, resorcinol, a bioplastic (e.g., polyhydroxybutyrate), or any higher-value product that can be produced by a microbe capable of converting one or more simple sugars a product of interest.

In one or more embodiments, the S. glucoliberatum PABB004 can transferred from an existing culture in which the simple sugar has accumulated to a fresh culture so that the S. glucoliberatum PABB004 can produce the simple sugar in the fresh culture medium. In one or more alternative embodiments, the simple sugar can be extracted from the S. glucoliberatum PABB004 culture (e.g., using a dialysis-style semipermeable membrane) to remove the simple sugar periodically or continually from the culture medium while keeping the algae inside the photobioreactor.

In one or more embodiments, the culture can have a pH of 6.2 or greater, 6.6 or greater, 7.0 or greater, 7.4 or greater, or 7.8 or greater. In one or more embodiments, the culture can have a pH of no greater than 8.5, no greater than 8.0, or no greater than 7.8. In one or more embodiments, the culture can have a pH that falls within a range having endpoints defined by any minimum pH listed above and any maximum pH listed above that is greater than the selected minimum pH. Thus, the culture can have a pH of 6.2 to 8.5, 6.2 to 8.0, 6.2 to 7.8, 6.6 to 7.8, 7.0 to 7.8, 7.0 to 8.5, etc. In one or more embodiments, the pH value of the culture can equal any minimum pH or maximum pH value listed above. Thus, for example, the culture can have a pH of 6.2, 7.8, 6.6, 8.5, etc.

This disclosure further describes a co-culture that includes S. glucoliberatum PABB004 and a second organism selected to produce a product of interest. The second organism can be a microbe—e.g., a bacterium, an archaeon, a fungus, or a yeast—that produces the product of interest either natively or as a result of being engineered to do so. In one or more embodiments, the co-culture can include a simple sugar produced by S. glucoliberatum PABB004 and which the second organism metabolizes in the process of making the product of interest. In one or more embodiments, the product of interest can be, but is not limited to, ethanol, a wax ester, a triacylglyceride, resorcinol, or a bioplastic (e.g., polyhydroxybutyrate).

Thus, in another aspect, this disclosure describes a method of biosynthesizing a product of interest. Generally, the method includes co-culturing S. glucoliberatum PABB004 with a microbe selected to produce the product of interest, wherein the culture has a pH of from 6.2 to 8.5. In one or more embodiments, the product of interest can be, but is not limited to, ethanol, a wax ester, a triacylglyceride, resorcinol, or a bioplastic (e.g., polyhydroxybutyrate).

In the preceding description and following claims, the term "and/or" means one or all of the listed elements or a combination of any two or more of the listed elements; the terms "comprises," "comprising," and variations thereof are to be construed as open ended i.e., additional elements or steps are optional and may or may not be present; unless otherwise specified, "a," "an," "the," and "at least one" are used interchangeably and mean one or more than one; and the recitations of numerical ranges by endpoints include all numbers subsumed within that range (e.g., 1 to 5 includes 1, 1.5, 2, 2.75, 3, 3.80, 4, 5, etc.).

In the preceding description, particular embodiments may be described in isolation for clarity. Reference throughout this specification to "one embodiment," "an embodiment," "certain embodiments," or "some embodiments," etc., means that a particular feature, configuration, composition, or characteristic described in connection with the embodiment is included in at least one embodiment of the disclosure. Thus, the appearances of such phrases in various places throughout this specification are not necessarily referring to the same embodiment of the disclosure. Furthermore, the particular features, configurations, compositions, or characteristics may be combined in any suitable manner in one or more embodiments. Furthermore, the particular features, configurations, compositions, or characteristics may be combined in any suitable manner in one or more embodiments. Thus, features described in the context of one embodiment may be combined with features described in the context of a different embodiment except where the features are necessarily mutually exclusive.

For any method disclosed herein that includes discrete steps, the steps may be conducted in any feasible order. And, as appropriate, any combination of two or more steps may be conducted simultaneously.

As used herein, the terms "preferred" and "preferably" refer to embodiments of the invention that may afford certain benefits under certain circumstances. However, other embodiments may also be preferred under the same or other circumstances. Furthermore, the recitation of one or more preferred embodiments does not imply that other embodiments are not useful and is not intended to exclude other embodiments from the scope of the invention.

The present invention is illustrated by the following examples. It is to be understood that the particular examples, materials, amounts, and procedures are to be interpreted broadly in accordance with the scope and spirit of the invention as set forth herein.

EXAMPLES

*Scenedesmus glucoliberatum* PABB004 Isolation and Culture Conditions

Natural isolates of *P. bursaria* were enriched by collecting 1 L of water from various lakes and ponds in the Minneapolis metro region and growing for several days under fluorescent lights. Initial medium was based on Bristol's recipe (Knutson et al., 2018, *Algal Res* 35:301-308) and contained 250 mg $NaNO_3$, 250 mg $K_2HPO_4$, 75 mg $MgSO_4 \cdot 7H_2O$, 25 mg $CaCl_2 \cdot H_2O$, 25 mg NaCl and 15 mg ferric ammonium citrate, all per liter, adjusted to pH 7.8. Medium was supplemented with two grains of rice or a single wheat seed (Gong et al., 2014, *Syst Appl Microbiol* 37(1):35-41) per 250 mL prior to autoclaving in a 500 mL Erlenmeyer flask and grown on a light table until *P. bursaria* were observed swimming in the medium. Aliquots of healthy *P. bursaria* were transferred several times to enrich until there were approximately 4 or 5 *P. bursaria* cells per 50 µL aliquot. Cultures were then spotted onto freshly prepared agar plates of freshwater SAG medium (Arriola et al., 2018, *Plant J* 93:566-586) as drops containing 2-3 µL of liquid, and drops containing *P. bursaria* were marked on the plate following visual inspection under a microscope. *P. bursaria* cells generally burst on the plate as the droplet evaporated or was absorbed into the plate, releasing the algae contained within. Algal cells derived from the broken *P. bursaria* that formed colonies were picked with sterile toothpicks, and carefully transferred to sterile media plates to isolate and purify the strains. Strains were passaged several times on solid agar plates until pure cultures were obtained. One strain, later designated *Scenedesmus glucoliberatum* PABB004 was selected for further studies.

Sugar Secretion Experiments

Sugar secretion experiments were conducted in stoppered 1.5 L tubular photobioreactors equipped with an inverted U-Tube exhaust tube to minimize external contamination using the same modified freshwater SAG medium as described previously (Arriola et al., 2018, *Plant J* 93:566-586), and supplemented with 10 mM each of MES, MOPS and PIPES, then brought to the desired pH. Culture pH levels were adjusted throughout the experiment on a semi-daily basis to maintain it within 0.1 pH units of the target value. In additional experiments, pH was maintained by growing on a proton-balanced medium that contained 1 mM $(NH_4)_2SO_4$ and 2 mM $NaNO_3$ as the nitrogen sources for the freshwater SAG medium. This medium did not require adjustment of the pH through the duration of the culture. Levels of extracellular glucose and maltose were analyzed enzymatically as described previously (Arriola et al., 2018, *Plant J* 93:566-586). Cells were monitored for potential contamination by inspection under a microscope and visual inspection of the algal cell pellets during sampling. The continued increase in sugar accumulation was also interpreted as an indication that contamination through the approach used to culture this alga were minimal.

Light and Scanning Electron Microscopy

Cells of *S. glucoliberatum* PABB004 cultivated on agar plates were harvested and prepared for microscopy imaging. For light microscopy 5 µL of algal suspension were mounted on alcohol-cleaned glass slides with a coverslip and sealed with dental wax. Images were acquired in a Nikon 90i microscope equipped with a Plan Apo VC 100× Oil DIC N2 1.4 NA objective and a DS-Fi2-U3 camera. The microscope and camera were controlled by Nikon Elements software (5.02). After adjusting the condenser for Kohler illumination, software was used to adjust the white balance. Images (24-bit RGB) were acquired with Auto exposure time and pixel resolution of 2560×1920 (fine, final pixel size 30 nm).

For scanning electron microscopy, samples were suspended in 2% gluteraldehyde and 0.1 M phosphate buffer, kept at 4° C. for at least 12 hours, and rinsed in 0.1 M phosphate buffer (3 times, 10 minutes each). Samples were then placed in 1% osmium tetroxide and 0.1 M phosphate buffer for two hours at room temperature. Specimens were rinsed in ultrapure water (NANOpure Infinity; Barnstead/Thermo Fisher Scientific; Waltham, Maryland) (3 times, 10 minutes each) and dehydrated in an ethanol series (50%, 75%, 95%, 100%; 5 minutes, 2 times each). After the samples were in 100% ethanol, they were put through two changes of hexamethyldisilazane (HMDS) for 5 minutes each. Drops of the suspension were placed on individual round glass cover slips cleaned with acetone, mounted on aluminum stubs, and allowed to air dry. The stubs were sputter-coated with gold-palladium (60-40) and observed in a Hitachi S3500N scanning electron microscope (Hitachi High Technologies America, Inc.; Schaumberg, Illinois) at an accelerating voltage of 10 kV.

Genomic DNA Isolation and Sequencing

Cells of *S. glucoliberatum* PABB004 grown on agar plates were used for total DNA isolation using the ZR Fungal/Bacterial DNA Microprep kit (Zymo Research, Irvine, CA) as directed by the manufacturer. Following isolation, DNA quantity and purity was measured with a NanoDrop 2000 spectrophotometer (Thermo Scientific, Inc., Waltham, MA).

Illumina sequencing was performed at the University of Minnesota Genomics Center, following the standard protocol for pair-end reads Illumina HiSeq 2500 (Illumina, San Diego, CA). Library preparation and long read sequencing was carried out by the Rochester Mayo Medical Genome Facility with PacBio SMRT-RS technology as previously described (Arriola et al., 2018, *Plant J* 93:566-586). Sequencing was done using 6 SMRT cells.

Genome Hybrid Assembly

PacBio long reads were assembled using Canu (Koren et al., 2017, *Genome Res* 27:722-736) version 1.8. Genome size was estimated through consecutive iterations of the assembly process with starting values ranging between 30 and 120 Mb. Contigs with negative covStat, as reported by Canu, were used as queries in BLASTn searches to look for and remove bacterial or PacBio contaminants. Mitochondrial DNA was manually circularized by aligning and clipping the contig overhangs. The resulting contig set was polished with Illumina short reads using Pilon version 1.22, with default parameters for seven iterations, when there were no more changes reported by the pipeline.

Assembly quality was assessed with N50 and L50 statistics, the proportion of PacBio reads that were used by Canu and the percent Illumina reads that mapped back to the assembly. Completeness was evaluated with BUSCO quality scores (BUSCO version 4.0.5) using the genomic mode and the chlorophyta_odb10 dataset (creation date Nov/20/2019), which contains 16 species and 1519 BUSCOs.

Additionally, each contig end was examined to calculate GC % and find repetitive regions. Contig ends with GC content below 50%, and 100% repetitive were marked as telomers and confirmed by manual inspection. Contigs with telomers $(TTTAGGG)_n$ on both ends were considered full chromosomes.

Repetitive regions were soft-masked with RepeatMasker version 4.0.5 using the available *Scenedesmus* repeat library (Smit et al., 2013, RepeatMasker Open-4.0. 2013-2015).

*S. glucoliberatum* PABB004 RNA Isolation, Sequencing, and Transcriptome Assembly

*S. glucoliberatum* PABB004 cells were harvested at midday after 5 days and after 13 days of cultivation, frozen in liquid nitrogen and stored at −80° C. until RNA extraction. Total RNA extraction was performed as described previously (Arriola et al., 2018, *Plant J* 93:566-586). Poly(A)+-tag based mRNA isolation and sequencing were conducted by the University of Minnesota Genomics Center. Poly(A)+ RNA was isolated with oligo (dT) magnetic beads and fragmented at elevated temperatures. Synthesis of cDNA used the fragmented mRNA as template and random primers. Additionally, a cDNA library was constructed by reverse PCR amplification of adapter-mRNA sequences. All cDNA was sequenced with HiSeq 2500 Illumina technology.

RNA reads were aligned to the genome using STAR version 6.06.017_01. The resulting alignment file (bam) was used to guide Trinity version 2.9.1 for a genome-guided de novo transcriptome assembly using the *S. glucoliberatum* PABB004 genome as reference.

Gene Annotation and Sequence Analysis

Gene annotation was carried out separately for the nuclear and organellar contigs. Nuclear genes were predicted using AUGUSTUS version 3.2.3 and following Basic Protocol 11 and Alternative Protocol 13 as described by the pipeline authors (Hoff and Stanke, 2018, *Current Protoc Bioinformatics*). The "*Chlamydomonas*" species was used for the prediction parameters. RNA reads aligned to the genome as described above were used to generate an intron hints file for AUGUSTUS. Chloroplast contigs were annotated using the online GeSeq prediction tool (Tillich et al., 2017, *Nucleic Acids Res* 45:W6-W11) with *Tetradesmus obliquus, Chlamydomonas reinhardtii*, and *Chlorella sorokiniana* as reference sequences for BLAT searches. The resulting gff3 files were manually inspected to remove duplicate features. Reading frame convention (column 8 of the gff3 tables) was changed from [1-3] to [0-2] to be in accordance with the AUGUSTUS output. Mitochondrial genes were predicted using Prodigal version 2.50 and selected based on sequence similarity searches using BLASTp.

Nuclear and organellar annotation gff3 files were joined and further polished based on the output discrepancy and validation reports given by table2asn. Briefly, the "transcript", "start_codon", "stop_codon" and "transcription_end_site" features were removed, duplicated, and contained features were filtered out and the mitochondrial genetic code was changed to *S. obliquus* Mitochondrial Code (transl_table=22).

Functional annotation was produced by comparing the translated *S. glucoliberatum* PABB004 predicted CDSs with the reviewed Swiss-Prot protein database through a BLASTp (version 2.8.1) search using an e-value of $1\times10^{-6}$ and selecting only the best-score hit for each protein. Protein names were given to the predicted CDSs based on these BLASTp results and manually curated following NCBI recommendations. Annotation quality was assessed with BUSCO version 4.0.5 using the protein mode and the chlorophyta_odb10 dataset.

The *S. glucoliberatum* PABB004 proteome was also examined through the KEGG annotation tool using default thresholds, BLASTp and BBH algorithms and the following GENES dataset: hsa, dme, cel, ath, sce, cho, eco, nme, hpy, rpr, bsu, lla, cac, mge, mtu, ctr, bbu, syn, bth, dra, aae, mja, ape, cre, mng, apro, olu, ota, mis, and mpp.

S. *glucoliberatum* PABB004 Phylogenetic Analysis

*S. glucoliberatum* PABB004 contigs were initially examined to find the SSU rRNA gene through a BLASTn search against green algae SSU rRNA genes. Then, a diverse dataset of SSU sequences from green algae was gathered to infer *S. glucoliberatum* PABB004 evolutionary history. This dataset contained representatives of the Chlorophyceae and Trebouxiophyceae clades among the green algae lineage and two bacterial SSU rRNA gene sequences (outliers). Data was downloaded from the SILVA and NCBI nucleotide databases. Only SSU sequences derived from PCR amplifications (not genomic segments) were used to avoid alignment issues with introns and gene prediction artifacts.

SSU rRNA sequences were aligned using MUSCLE (UPGMA clustering, gap opening penalty −400 and no gap extension penalty) to remove *S. glucoliberatum* PABB004 overhangs as previously described (Hoshina et al., 2010, *Phycol Res* 58:188-201). The final sequence set was aligned again using the same strategy and an evolutionary analysis was conducted in MEGA X (Kumar et al., 2018, *Mol Biol Evol* 35:1547-1549). A Maximum Likelihood analysis with the Kimura 2-parameter model was chosen to estimate evolutionary distances (Kimura, M., 1980, *J Mol Evol* 16:111-120) as suggested by MEGA X Best Model Tool. The bootstrap consensus phylogenetic tree was inferred from 100 replicates. Branches corresponding to partitions reproduced in less than 50% bootstrap replicates were collapsed. Initial tree(s) for the heuristic search were obtained automatically by applying Neighbor-Join and BioNJ algorithms to a matrix of pairwise distances estimated using the Maximum Composite Likelihood (MCL) approach, and then selecting the topology with superior log likelihood value. A discrete Gamma distribution was used to model evolutionary rate differences among sites (2 categories (+G, parameter=0.5045)) on a total of 3580 positions (gaps included) in the final dataset. Tree image was prepared with the web iTOL tool (Letunic, I. and Bork, P., 2019, *Nucleic Acids Res* 47:W256-W259).

S. *glucoliberatum* PABB004 Phylogenomic Analysis

To have a better understanding of *S. glucoliberatum* PABB004's origin, an Average Nucleotide Identity (ANI) analysis was performed using its transcriptome and transcriptomic data from Chlorophyceae and Trebouxiophyceae algae. Transcriptomes were analyzed using GET_HOMOLOGUES_EST (Contreras-Moreira et al., 2017, *Front Plant Sci* 8:143) version 25082020. Briefly, transcripts were clustered (OrthoMCL version 1.4) based on sequence similarity with sequences showing at least 70% nucleotide identity and 75% sequence coverage classified on the same cluster. Sequence similarity was calculated from BLASTn searches with an e-value threshold of $1\times10^{-5}$. Sequence clusters present in all taxa (i.e., that had at least one transcript from each species) were used to calculate the percent average nucleotide identity among pairs of organisms.

Proteomic Comparisons

To explore the molecular basis of the sugar secretion phenotype in algae, the predicted proteomes of two sugar-secreting organisms (*S. glucoliberatum* PABB004 and *M. conductrix*) and two non-sugar secretors (*C. reinhardtii* and *C. sorokiniana*) were compared using OrthoVenn2 (Xu et al., 2019, *Nucleic Acids Res* 47:W52-W58). In detail, the curated proteomes from *M. conductrix, C. sorokiniana* and *C. reinhardtii* were downloaded from the Swissprot-Uniprot database (accession numbers UP000239649, UP000239899 and UP000006906, respectively) and all protein sequences including *S. glucoliberatum* PABB004's were clustered using DIAMOND version 0.9.24 with an e-value threshold of $1\times10^{-10}$ and the OrthoMCL algorithm with an inflation value of 1.5. The protein set shared by *M. conductrix* and *S. glucoliberatum* PABB004 and absent from the other alga was analyzed for its potential relationship with sugar-secretion mechanisms. This potential sugar-related subset of proteins was further examined with BLASTp searches against the NCBI non-redundant and InterProScan v5.23-62.0 databases.

The complete disclosure of all patents, patent applications, and publications, and electronically available material (including, for instance, nucleotide sequence submissions in, e.g., GenBank and RefSeq, and amino acid sequence submissions in, e.g., SwissProt, PIR, PRF, PDB, and translations from annotated coding regions in GenBank and RefSeq) cited herein are incorporated by reference in their entirety. In the event that any inconsistency exists between the disclosure of the present application and the disclosure(s) of any document incorporated herein by reference, the disclosure of the present application shall govern. The foregoing detailed description and examples have been given for clarity of understanding only. No unnecessary limitations are to be understood therefrom. The invention is not limited to the exact details shown and described, for variations obvious to one skilled in the art will be included within the invention defined by the claims.

Unless otherwise indicated, all numbers expressing quantities of components, molecular weights, and so forth used in the specification and claims are to be understood as being modified in all instances by the term "about." Accordingly, unless otherwise indicated to the contrary, the numerical parameters set forth in the specification and claims are approximations that may vary depending upon the desired properties sought to be obtained by the present invention. At the very least, and not as an attempt to limit the doctrine of equivalents to the scope of the claims, each numerical parameter should at least be construed in light of the number of reported significant digits and by applying ordinary rounding techniques.

Notwithstanding that the numerical ranges and parameters setting forth the broad scope of the invention are approximations, the numerical values set forth in the specific examples are reported as precisely as possible. All numerical values, however, inherently contain a range necessarily resulting from the standard deviation found in their respective testing measurements.

All headings are for the convenience of the reader and should not be used to limit the meaning of the text that follows the heading, unless so specified.

What is claimed is:

1. A co-culture comprising:
   culture medium comprising a carbon source;
   S. glucoliberatum PABB004, wherein the S. glucoliberatum PABB004 secretes at least one simple sugar into the culture medium in the presence of the carbon source; and
   a second organism, wherein the second organism is a microbe that can feed on the simple sugars secreted by the S. glucoliberatum PABB004 into the culture medium;
   wherein co-culture has a pH of 6.0 or greater.

2. The co-culture of claim 1, wherein the pH of the co-culture is 6.6 or greater.

3. The co-culture of claim 1, wherein the second organism is selected to produce at least one product of interest.

4. The co-culture of claim 3, wherein the product of interest is ethanol.

5. The co-culture of claim 1, wherein the simple sugar is glucose or maltose.

6. The co-culture of claim 1, wherein the second organism is a microbe.

7. The co-culture of claim 1, wherein the second organism is a bacterium.

8. The co-culture of claim 1, wherein the second organism is a yeast.

9. The co-culture of claim 1, wherein the second organism is a fungus.

10. The co-culture of claim 1, wherein the second organism is an archaeon.

11. The co-culture of claim 3, wherein the at least one product of interest comprises a wax ester, a triacylglyceride, resorcinol, or a bioplastic.

12. The co-culture of claim 11, wherein the bioplastic comprises polyhydroxybutyrate.

* * * * *